(12) United States Patent
Kolk et al.

(10) Patent No.: US 10,342,947 B2
(45) Date of Patent: Jul. 9, 2019

(54) FLEXIBLE, EXTENSIBLE, COAXIAL TYPE TUBE SYSTEM

(71) Applicant: Drägerwerk AG & Co. KGaA, Lübeck (DE)

(72) Inventors: Stefan Kolk, Gross Grönau (DE); Florian Dietz, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 890 days.

(21) Appl. No.: 14/813,583

(22) Filed: Jul. 30, 2015

(65) Prior Publication Data

US 2016/0030698 A1 Feb. 4, 2016

(30) Foreign Application Priority Data

Jul. 31, 2014 (DE) .................. 10 2014 011 188

(51) Int. Cl.
*A61M 16/08* (2006.01)
*A61M 39/08* (2006.01)

(52) U.S. Cl.
CPC .... *A61M 16/0883* (2014.02); *A61M 16/0875* (2013.01); *A61M 39/08* (2013.01); *A61M 2039/082* (2013.01); *A61M 2206/18* (2013.01); *A61M 2207/00* (2013.01)

(58) Field of Classification Search
CPC .......... F16L 11/20; F16L 11/115; F16L 11/00; F16L 11/08; F16L 11/088; F16L 11/10; F16L 11/11; F16L 11/111; F16L 11/112; F16L 11/14; F16L 11/15; F16L 11/18; F16L 11/22; F16L 11/24; A62B 7/00; A61M 16/0875; A61M 16/0883; A61M 16/08; A61M 16/0666; A61M 2039/082; A61M 39/08; A61M 2206/18; A61M 2207/00; A61M 2206/10; A61M 2206/14
USPC ...................................... 128/204.18
See application file for complete search history.

(56) References Cited

U.S. PATENT DOCUMENTS

| | | | |
|---|---|---|---|
| 3,856,051 A * | 12/1974 | Bain | A61M 16/009 128/203.12 |
| 4,621,634 A * | 11/1986 | Nowacki | A61M 16/08 128/204.18 |
| 4,838,258 A * | 6/1989 | Dryden | A61M 16/0816 128/204.18 |
| 4,967,744 A | 11/1990 | Chua | |
| 6,032,699 A * | 3/2000 | Cochran | B67D 7/3209 138/104 |

(Continued)

FOREIGN PATENT DOCUMENTS

| | | |
|---|---|---|
| CN | 1309946 A | 8/2001 |
| CN | 103791179 A | 5/2014 |

(Continued)

*Primary Examiner* — Jan Christopher L Merene
*Assistant Examiner* — Elliot S Ruddie
(74) *Attorney, Agent, or Firm* — McGlew and Tuttle, P.C.

(57) ABSTRACT

A tube system for ventilation with an outer tube (1) and with an inner tube (3) arranged non-centrally in the radial direction in the interior of the outer tube (1) is shown and described. The coaxial type tube system may be provided for ventilation and for medical applications. The flow resistance for the gas is minimized by the inner tube (3) being designed such that it is linearly in contact with an inner wall (35) of the outer tube (1).

7 Claims, 3 Drawing Sheets

(56) References Cited

U.S. PATENT DOCUMENTS

| | | | |
|---|---|---|---|
| 6,874,500 B2* | 4/2005 | Fukunaga | A61M 16/00 128/203.12 |
| 7,077,165 B2* | 7/2006 | Takasaki | F16L 9/18 138/108 |
| 2001/0017163 A1* | 8/2001 | Penza | F16L 11/20 138/98 |
| 2001/0017164 A1 | 8/2001 | Fukui et al. | |
| 2002/0036019 A1* | 3/2002 | Woelfel | F16L 11/22 138/115 |
| 2005/0150505 A1* | 7/2005 | Burrow | A61M 16/0816 128/204.18 |
| 2014/0102452 A1 | 4/2014 | Forrester | |
| 2014/0130931 A1* | 5/2014 | Forrester | F16L 11/115 138/122 |

FOREIGN PATENT DOCUMENTS

| | | |
|---|---|---|
| DE | 296 02 060 U1 | 3/1996 |
| DE | 296 01 293 U1 | 4/1996 |
| DE | 203 16 465 U1 | 3/2004 |
| EP | 0574371 A1 | 12/1993 |
| EP | 0579384 A1 | 1/1994 |
| GB | 1 419 841 A | 12/1975 |

* cited by examiner

FLEXIBLE, EXTENSIBLE, COAXIAL TYPE TUBE SYSTEM

CROSS REFERENCE TO RELATED APPLICATIONS

This application claims the benefit of priority under 35 U.S.C. § 119 of German Patent Application 10 2014 011 188.1 filed Jul. 31, 2014, the entire contents of which are incorporated herein by reference.

FIELD OF THE INVENTION

The present invention pertains to a flexible, extensible, coaxial tube system, especially for ventilating patients with ventilation systems.

BACKGROUND OF THE INVENTION

Tube systems for ventilation (also known as respiration) with two separate tube volumes extending in parallel have been sufficiently well known from the state of the art. They are used preferably in the field of medicine, especially for the purposes of ventilating patients, and they have an inspiratory line and an expiratory line connected to it, which facilitates the use.

For example, it is known from the state of the art that two ventilation lines that are separated from one another can be provided by a tube with an axially extending, membrane-like partition being provided, so that two volumes that are separated from one another are generated thereby. However, the length of the tube system is defined as a fixed value in this variant (for example, Limb-O variant of Vital Signs).

The tube system may also be designed as a coaxial tube system with an outer tube and an inner tube with a smaller diameter, and both tubes are usually designed as corrugated tubes in order to ensure the necessary flexibility. Furthermore, coaxial tube systems are known as well, whose length is variable. This property of a variable tube length is achieved by the outer tube and the inner tube being designed each as a folded tube, in which the folds spread out during longitudinal extension. Coaxial tube systems with the possibility of varying the length have the advantage over tube systems with fixed lengths that tube systems with different lengths are not needed for different applications, and, for example, the storage expenses of a medical institution is not increased due to the need to stock the tube systems in a plurality of lengths. Furthermore, situations in which a flexible length adaptation is desirable, for example, when changing the position of patients, may occur during the use of the tube systems.

However, the tubes are connected to one another at their respective ends only in the coaxial tube systems with outer tube and inner tube and are in an undefined position in relation to one another between the ends. The coaxial tube systems with fixed or variable length known from the state of the art have the following drawback due to this design. First, the often sharp-edged folds of the inner tube and of the outer tube, which are needed for the flexibility and possibly for extensibility, generate a turbulent flow of the gas in areas in which the gap between the inner tube and the outer tube does not reach a critical value, which will then lead, on the whole, to an increased flow resistance for the gas.

SUMMARY OF THE INVENTION

Therefore, based on the state of the art, an object of the present invention is to provide a coaxial type tube system, especially for ventilation and for medical applications, in which the flow resistance for the gas is minimized.

This object is accomplished according to the present invention by a coaxial type tube system with an outer tube and with an inner tube arranged non-centrally in the interior of the outer tube in the radial direction, wherein the inner tube is designed such that it is linearly in contact with an inner wall of the outer tube.

It is guaranteed hereby that the width of the radial gap between the inner tube and the inner wall of the outer tube is maximized in the radial direction opposite the side on which the inner tube is linearly in contact with the outer tube. It is avoided hereby, in particular, that the width of the gap drops below a critical value, below which turbulences, which develop on the profiled surfaces of the tubes, cause a massive increase in the flow resistance for the breathing gas in the intermediate space between the inner tube and the outer tube.

The outer tube and the inner tube preferably have ends, and the ends of the outer tube are firmly connected to the ends of the inner tube. The positions of the outer tube and inner tube relative to one another are thus preset permanently.

Furthermore, it is advantageous if the tube system has an outer tube and an inner tube, whose length is variable. The tube system can be adapted s a result to changed situations during the use of the tube system.

Furthermore, it is preferred that the inner tube is designed such that it is under a prestress in the axial direction, which contracts the inner tube in the axial direction. It is achieved hereby that with the ends of the inner tube being arranged eccentrically at the outer tube, the inner tube is always in contact with the outer tube, because it seeks to minimize its length, so that a linear contact will become established in this manner between the outer tube and the inner tube.

In a preferred embodiment, the inner tube has, in the longitudinal section, V-shaped sections and intermediate sections, which are located between the V-shaped sections and adjoin the free ends of the V-shaped sections. The tip of the V-shaped sections faces radially to the outside, while the intermediate sections are straight on the side facing the tube axis, and they have a curved shape to the outside, which protrudes radially to the outside to the same extent as the V-shaped sections. This makes a longitudinal extension possible due to the spreading out of the V-shaped sections, and the straight inner sides and the curved outer sides of the intermediate sections bring about a low flow resistance in both the inner tube and the intermediate space between the inner tube and the outer tube.

The intermediate sections and the sections that are V-shaped in the longitudinal section for longitudinal extension may have a ring-shaped cross section. It is also conceivable that the intermediate sections and the sections having a V-shaped longitudinal section have a helical design in the axial direction between the ends of the inner tube.

In another preferred embodiment, the profile of the inner tube has strips in the longitudinal section, which extend radially from the inside to the outside and are flatly connected to one another at their ends alternatingly at the top and at the bottom. The inner tube consequently comprises ring-shaped elements in the cross section. An inner tube with prestress in the longitudinal direction, where the outwardly facing connection sections of the strips can come to lie in corresponding recesses in the wall of the outer tube, can be designed in this manner as well.

In another preferred embodiment, the inner tube has a spring element, which extends helically along the inner tube between the ends. A prestress, which contracts the tube in the axial direction and thus leads to a linear contact of the inner tube with the outer tube in the above-described manner, is generated by this spring element in the inner tube.

Furthermore, it is preferred that an intermediate section consisting of a flexible material, which is bellows-like (bellows-shaped) in the longitudinal section of the inner tube, is formed in the inner tube between adjacent turns of the helical spring element, wherein the length of the flexible material between two adjacent turns in the axial direction of the inner tube corresponds to a multiple of the distance between two adjacent turns of the spring element in case of maximum longitudinal extension of the inner tube, wherein the diameter of the intermediate section corresponds to the external diameter of the inner tube, and wherein the folds of the intermediate section are in contact with the spring element radially on the outside. An inner tube designed in this manner has a great longitudinal extension potential, and the folds that are in contact cover the turns of the helical spring element even in case of an increased tube length. As a result, the inner tube has a smooth surface without sharp edges or tips, which could increase the flow resistance due to turbulences.

In another preferred embodiment, the inner tube and the outer tube are also connected to one another in a positive-locking manner at an additional point between the ends of the tubes, in addition to their connection at the ends. It is also conceivable that the inner tube and the outer tube are connected to one another linearly by welding. A connection can also be established between the outer tube and the inner tube in this manner, for example, also by locking, as a consequence of which a linear contact will develop between the outer tube and the inner tube.

According to another preferred embodiment, the outer tube and the inner tube have, in the longitudinal section, a folded contour, which is formed in the longitudinal direction alternatingly from a flank sloped in relation to the longitudinal direction and a radially outwardly extending flank. A radially outwardly extending flank of the folded contour of the inner tube is connected with a radially outwardly extending flank of the folded contour of the outer tube along a line extending in the longitudinal direction of the tube. The inner tube is connected in this manner to the outer tube over the entire length and forms a gap, whose width is maximized over the entire length of the tube, between the inner tube and the outer tube, as a result of which the flow resistance is reduced.

The present invention will be explained below on the basis of a drawing showing only preferred exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
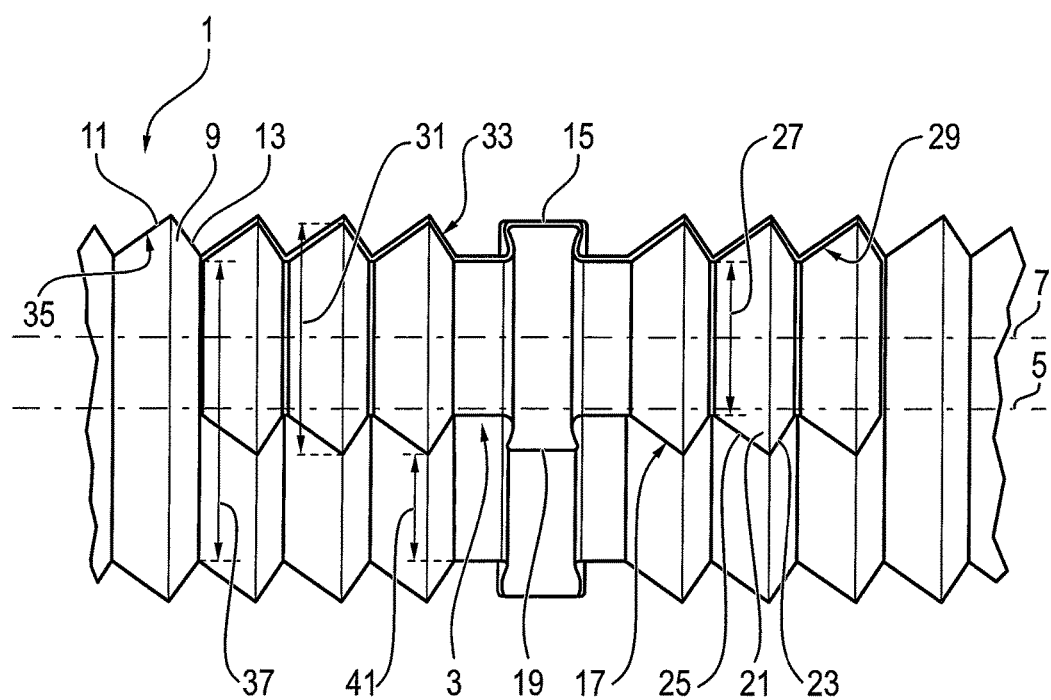
FIG. 1 is a longitudinal sectional view of a first exemplary embodiment of a coaxial type tube system according to the present invention.
Figure 2:
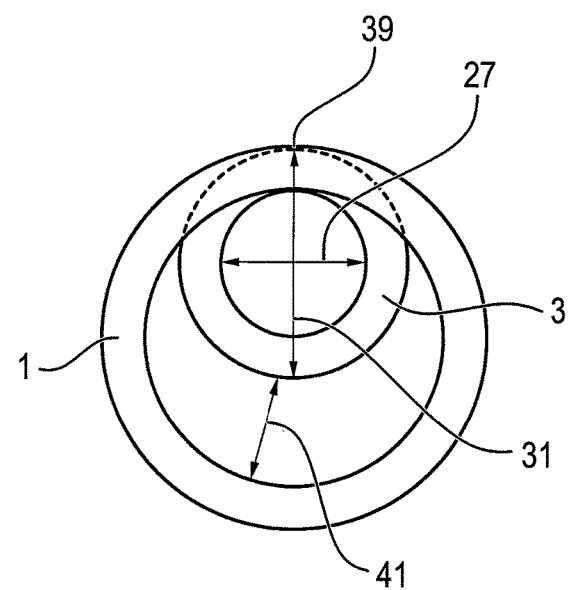
FIG. 2 is a cross sectional view of the exemplary embodiment from FIG. 1.

Referring to the drawings, FIG. 1 shows a first exemplary embodiment of a coaxial type tube system in a longitudinal section, while FIG. 2 shows the cross section of this tube system.

It can be seen in these two views that the tube system has an outer tube 1 and an inner tube 3, and the outer tube 1 has a symmetry axis 5 and the inner tube 3 has a symmetry axis 7. These two symmetry axes 5, 7 are located at spaced locations from one another, so that the inner tube 3 is arranged eccentrically in the outer tube 1. The outer tube 1 has folds 9 with two flanks 11, 13 each, which spread out during the extension of this variable-length tube system.

In addition to the folds 9, the outer tube 1 has in this embodiment a groove-like profile 15, which extends circumferentially around the outer tube 1 and which is connected to a profile 19 extending circumferentially around the inner tube 3 on the radially outwardly directed outer side 17 of the inner tube 3 by locking in a positive-locking manner. This positive-locking connection of the profiles 15, 19 may be repeated several times at preset spaced locations over the entire length of the tube. However, these additional possible connection points of additional profiles 15, 19 are not shown in the detail view of the tube system, which is shown in FIG. 1.

Just like the outer tube 1, the inner tube 3 has folds 21 in the exemplary embodiment being shown here for changing the length, these folds being formed from two flanks 23, 25, which spread out during pulling apart. The internal diameter 27 of the inner tube 3 is formed by the smallest distance of the radially inwardly facing inner wall 29. The external diameter 31 of the inner tube 3 is formed by the greatest distance of the radially outwardly facing outer side 33.

The outer tube 3 has a radially inwardly directed inner wall 35, whose smallest distance forms an internal diameter 37 of the outer tube.

The inner tube 3 is in contact with the inner wall 35 of the outer tube 1 along a connection line 39 with its outer side 17 because of the meshing of the profiles 15, 19.

As can be seen in FIG. 1 and even more clearly in the cross section shown in FIG. 2, a gap 41, whose width is formed by the distance between the external diameter 31 of the inner tube 3 and the internal diameter 37 of the outer tube 1, is formed on the side of the inner tube 3 that is located opposite the connection line 39. It should be noted in this connection that the gap 41 has a constant maximum width over the entire length of the tube. It is achieved due to this broad gap 41 that the flow resistance for the gas flowing through the outer tube 1 is minimized. In particular, the inner tube is prevented from being able to be arranged freely in the interior of the outer tube 1 by the linear contact of the inner tube 3 with the outer tube 1, so that even though the overall cross section would remain the same for the flow in the outer tube 1, a narrower gap would be formed between the outer tube 1 and the inner tube 3, which would lead to an increased flow resistance, especially because of the folds 9, 21 in both tubes.

Figure 3:
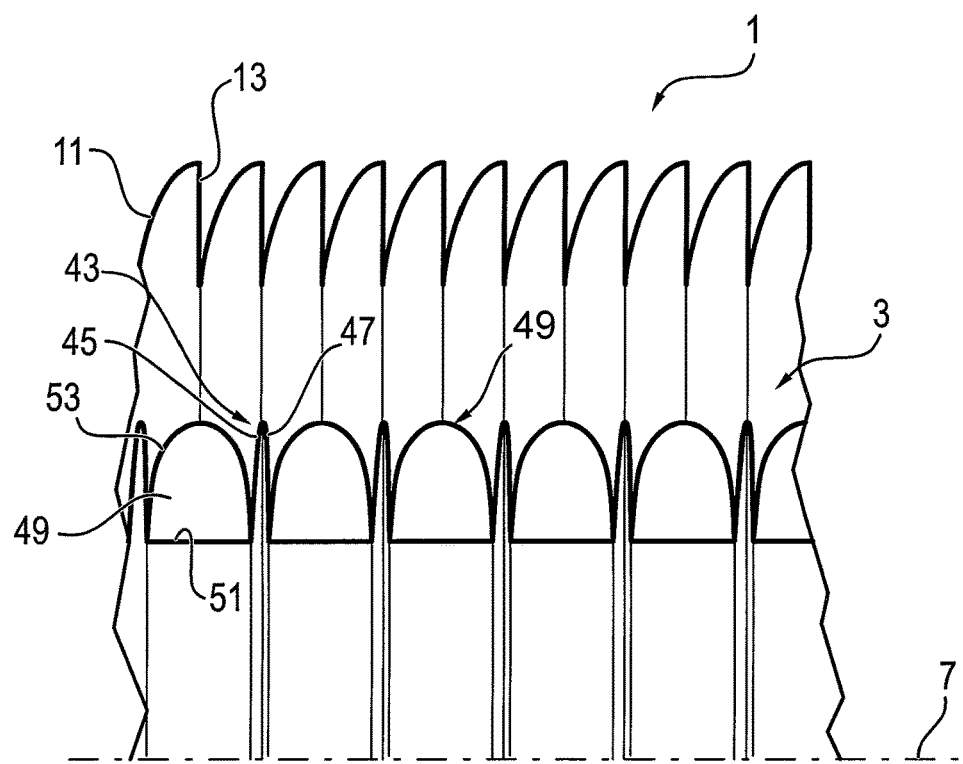
FIG. 3 is a partial longitudinal sectional view of a second exemplary embodiment of a coaxial type tube system according to the present invention.

As was already described above, the extensible outer tube 1 is again designed as a folded tube in the exemplary embodiment of a coaxial type tube system shown in FIG. 3. The inner tube 3, whose length can likewise be increased, has V-shaped sections 43 in the longitudinal sections, and the tips of these V-shaped sections are directed radially outwardly. The legs 45, 47 of the V-shaped sections 43 form an angle. The angle formed by the legs 45, 47 is an acute angle in this preferred exemplary embodiment and equals about 15° in the relaxed state of the inner tube 1. An intermediate section 49 each is arranged between all V-shaped sections 43. In the relaxed state of the inner tube 1, the intermediate sections 49 have a length in the longitudinal direction of the tube that is a multiple of the open distance between the legs 45, 47 of the V-shaped sections 43 without extension of the inner tube. The intermediate sections 49 are straight on the inner side 51 facing the symmetry axis 7 of the inner tube 3, and the radially outwardly facing side 53 has a curved shape. This curved outer side 53 projects radially to the outside by the same amount as the V-shaped sections 43. The free ends of the legs 45, 47 of the V-shaped sections 43 adjoin the intermediate sections 49 on the inner side 51 thereof. This makes possible a longitudinal extension by spreading out the V-shaped sections 43, and the straight inner sides 51 and the curved outer sides 53 of the intermediate sections 49, whose shape does not change during an extension, ensure that there will be hardly any change in the flow resistance in both the inner tube 3 and the outer tube 1.

It should be mentioned in this connection that the profiles of the V-shaped sections 43 and of the intermediate sections 49, which profiles are shown in the longitudinal section, may either have a ring-shaped cross section or a helical design in the axial direction. A restoring force of the inner tube 3 against extension or a corresponding prestress in the axial direction is achieved due to the elasticity of the V-shaped sections 43.

Figure 4:
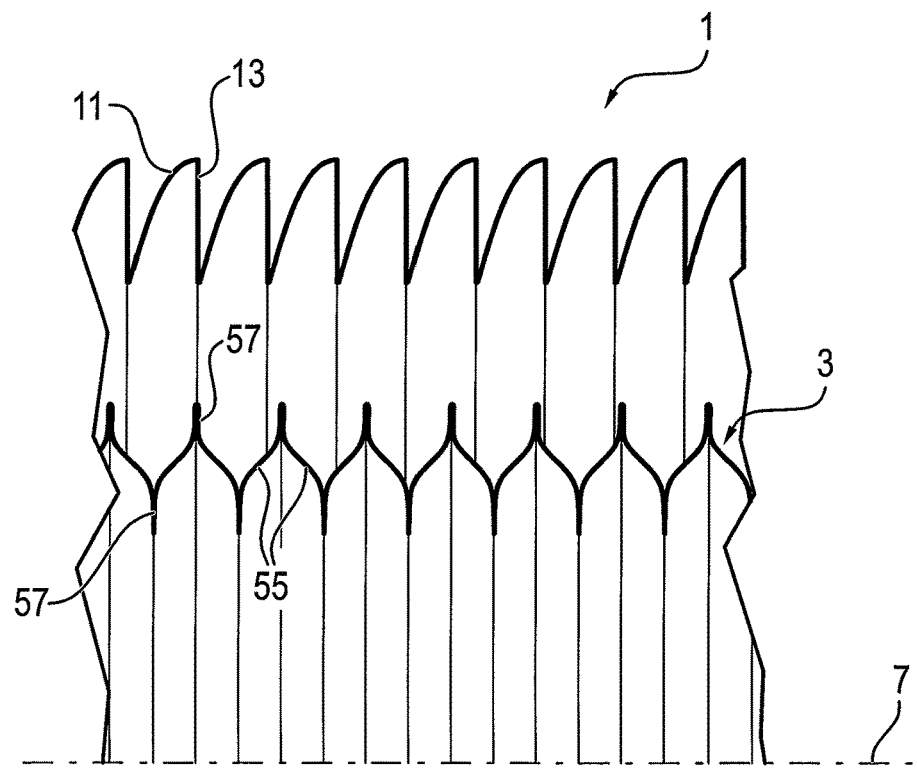
FIG. 4 is a partial longitudinal sectional view of a third exemplary embodiment of a coaxial type tube system according to the present invention.

As was already described above, the extensible outer tube 1 is again designed as a folded tube in the exemplary embodiment according to FIG. 4. The likewise extensible inner tube 3 has ring-shaped elements, which are flatly connected to one another alternatingly at the top and at the bottom.

This is embodied in the longitudinal section being shown by the strips 55, which extend radially from the inside to the outside and are connected to one another flat alternatingly at the top and at the bottom. Due to the rigid, flat connection points 57 at the ends of the strips 55, the strips 55 are slightly bent when pulled apart, which leads to an elasticity and hence to a restoring force against an extension or prestress in the axial direction if the strips 55 are made of a suitable material.

Figure 5:
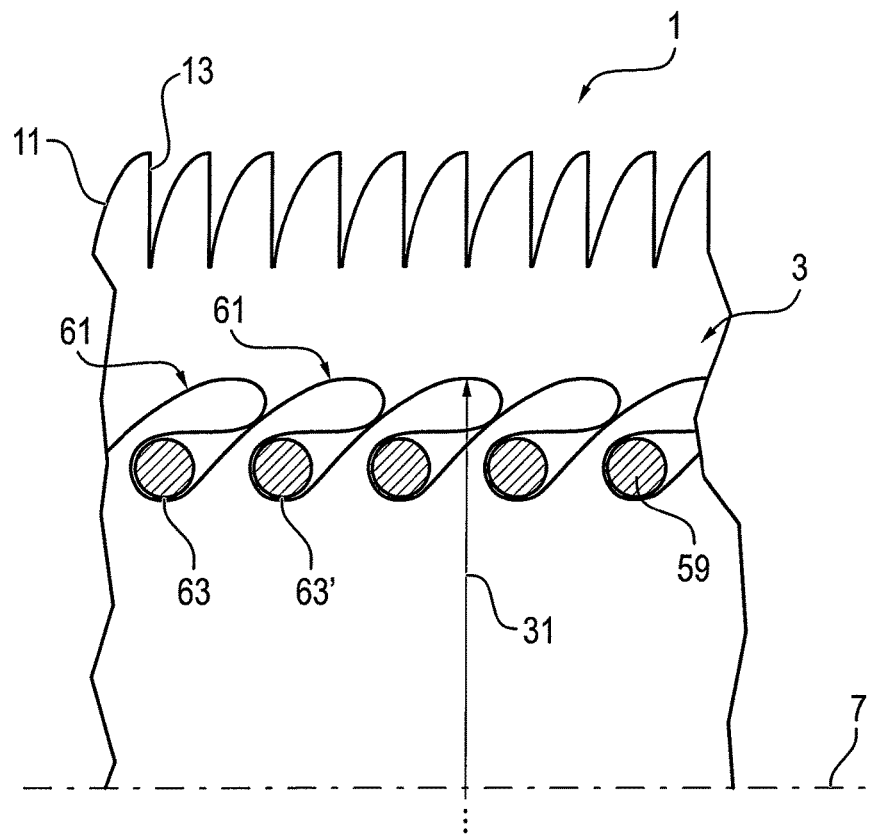
FIG. 5 is a partial longitudinal sectional view of a fourth exemplary embodiment of a coaxial type tube system according to the present invention.

As was already described above, the outer tube 1 is again designed as a folded tube in the embodiment shown in FIG. 5. The longitudinal section shows the inner tube 3 with a spring element 59 having a helical design in the axial direction, but the helical design of the spring element 59 cannot be shown in the longitudinal section. The turns of the spring element 59 are arranged at spaced locations from one another, and bellows-like intermediate sections 61 made of a flexible material are formed in the intermediate spaces of the turns. The bellows-like intermediate sections 61 are connected to the turns of the spring element 59 and are in contact with the spring element 59 on the outside. The bellows-like intermediate sections 61 are designed such that in the axial direction they have an overall length that corresponds to a multiple of the distance between two adjacent turns of the spring element 59 at maximum longitudinal extension of the inner tube 3. The bellows-like intermediate sections 61 extend from a first connection point 63 with a turn of the spring element 59 axially in the direction of an adjacent turn, and the bellows-like intermediate sections 61 extend, bent slightly to the outside, past the adjacent turn and then back again from there in the direction of the connection point 63, in order to be then connected to the adjacent turn at another connection point 63'. However, it should be noted here that all the connection points 63, 63' are located on a contiguous line because of the helical course of the spring element 59.

The diameter of the intermediate section 61 corresponds to the external diameter 31 of the inner tube, and the folds of the intermediate sections 57 are in contact with the spring element 59 radially on the outside. Because of their length, they cover the spring element 59 even when the inner tube 3 is in the extended state, so that a smooth outer side 17 is formed, which ensures s low flow resistance in the outer tube 1.

While only one spring element 59 is provided in the exemplary embodiment shown in FIG. 5, it is also conceivable that a double helix is used, in which case the second spring element of the double helix is received in the bellows-like intermediate sections 61 and ensures that these extend in the longitudinal direction and are tightly in contact with the first spring element.

In the above-described exemplary embodiments according to FIGS. 3 through 5, the linear contact of the inner tube 3 in the inner wall 35 of the outer tube 3 during the operation is brought about solely by the prestress in the inner tube 3, which arises from the elastic design and causes the inner tube 3 to seek to minimize its length. The inner tube 3 is therefore in contact with the inner wall 35, especially in case of a curved course of the entire tube system.

Figure 6:
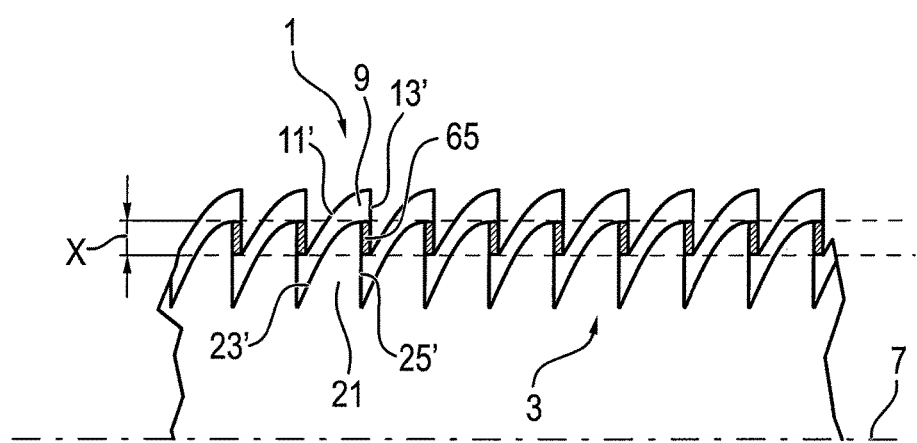
FIG. 6 is a partial longitudinal sectional view of a fifth exemplary embodiment of a coaxial type tube system according to the present invention.

As was already described above, the outer tube 1 is designed as a folded tube in the exemplary embodiment according to FIG. 6 and has folds 9, which are formed from two flanks 11' and 13'. The inner tube 3 likewise has folds 21 in the longitudinal section, which are formed from two flanks 23', 25'. The folds 9, 21 are pushed one into the other in the correct position in the embodiment being described here, so that one fold 21 of the inner tube 3 always protrudes into a fold 9 of the outer tube 1. Every other fold 13' of the folds 9 of the outer tube 1 and every other flank 25' of the folds 21 of the inner tube 3 extend radially from the inside to the outside, while the other flanks 11', 23' may be oblique in relation hereto or curved.

The folds 21 of the inner tube 3 are pushed into the folds 9 of the outer tube 1 to the extent that an overlapping area 65 of the folds 13' and 25' is formed, which extends from the radially outer end of the flank 25' of the folds 21 of the inner tube 3 to the radially inner end of the flank 13' of the folds 9 of the outer tube 1. The inner tube 3 is connected to the outer tube 1 in a suitable manner, especially by bonding or welding, at this overlapping area 65 in the embodiment being shown here, so that a linear and in this case permanent contact is established hereby.

A linear contact of the inner tube 3 with the inner wall 35 of the outer tube 3 is achieved in all exemplary embodiments, be it by positive-locking connection (FIGS. 1 and 2) or prestress (FIGS. 3 through 5) or by permanent connection such as welding or bonding (FIG. 6), so that the width of the gap between the inner tube 3 and the outer tube 1 is maximum. This in turn leads to a minimization of the flow resistance in the outer tube 1.

While specific embodiments of the invention have been shown and described in detail to illustrate the application of the principles of the invention, it will be understood that the invention may be embodied otherwise without departing from such principles.

What is claimed is:

1. A tube system for ventilation, the tube system comprising: an outer tube comprising a folded contour in a longitudinal direction of the outer tube, the folded contour being formed alternatingly from a curved flank or a bent flank in relation to the longitudinal direction and a radially outwardly extending straight flank in the longitudinal direction; an inner tube arranged non-centrally, in a radial direction, in an interior of the outer tube, wherein the inner tube is designed such that the inner tube is linearly in contact with an inner wall of the outer tube, wherein the inner tube has, in a longitudinal section, V-shaped sections, whose tip faces radially outwardly, and intermediate sections, which are located between the V-shaped sections and adjoin free ends of the V-shaped sections, wherein the intermediate sections are straight on a side facing a tube axis and have a curved shape towards an outside, which curve shape protrudes radially to a same extent as the V-shaped sections, each of the intermediate sections having an outer intermediate surface and each of the V-shaped sections having a V-shaped outer surface, the outer tube having an inner surface, the V-shaped outer surface, the outer intermediate surface and at least a portion of the inner surface defining at least a portion of a fluid flow channel, wherein the intermediate sections and the V-shaped sections have a ring-shaped cross section, each tip of the V-shaped sections is radially opposite a respective radially outwardly extending straight flank, each of the intermediate sections being located between one of the V-shaped sections and another one of the V-shaped sections, wherein each of the intermediate sections is radially opposite two curved flanks or two bent flanks in relation to the longitudinal direction and one said radially outwardly extending straight flank.

2. A tube system in accordance with claim 1, wherein:
the outer tube and the inner tube have ends;
each radially outwardly extending straight flank is perpendicular to a longitudinal axis of the outer tube; and
the ends of the outer tube are firmly connected to the ends of the inner tube.

3. A tube system in accordance with claim 2, wherein the inner tube is designed such that the inner tube is under a prestress in an axial direction, which contracts the inner tube in the axial direction.

4. A tube system in accordance with claim 1, wherein the outer tube and the inner tube have a variable length.

5. A tube system in accordance with claim 1, wherein the intermediate sections and the V-shaped sections are formed helically in the axial direction between the ends of the inner tube.

6. A ventilation tube system comprising: an outer tube having an interior and a folded contour in a longitudinal direction of the outer tube, the folded contour comprising a plurality of curved or bent flanks and a plurality of radially outwardly extending straight flanks, each of the curved or bent flanks being curved or bent in relation to the longitudinal direction, each of the radially outwardly extending straight flanks extending straight in a radial direction relative to the longitudinal direction, each of the radially outwardly extending straight flanks being located directly adjacent to one of the curved or bent flanks; and an inner tube arranged in the interior of the outer tube and non-centrally with respect to the radial direction, the inner tube having an outer wall linearly in contact with an inner wall of the outer tube, the outer tube and the inner tube having: ends, the ends of the outer tube being firmly connected to the ends of the inner tube, each of the radially outwardly extending straight flanks being perpendicular to a longitudinal axis of the outer tube, each of the outer tube and the inner tube being extensible, whereby a length of the outer tube and the inner tube between the connected ends of the outer tube and the inner tube may be varied, wherein the inner tube has, in a longitudinal section, V-shaped sections, whose tip faces radially outwardly, and intermediate sections, which are located between the V-shaped sections and adjoin free ends of the V-shaped sections; and the intermediate sections are straight on a side facing a tube axis and have a curved shape towards an outside, which curve shape protrudes radially to a same extent as the V-shaped sections, wherein the intermediate sections and the V-shaped sections having a ring-shaped cross section, each of the intermediate sections being adjacent to a first one of the V-shaped sections and a second one of the V-shaped sections, the tip of the first one of the V-shaped sections being radially opposite a first one of the radially outwardly extending straight flanks, the tip of the second one of the V-shaped sections being radially opposite a second one of the radially outwardly extending straight flanks, wherein a first one of the curved or bent flanks, a second one of the curved or bent flanks and a third one of the radially outwardly extending straight flanks are arranged between the first one of the radially outwardly extending straight flanks and the second one of the radially outwardly extending straight flanks, one of the intermediate sections being located between the first one of the radially outwardly extending straight flanks and the second one of the radially outwardly extending straight flanks, wherein the one of the intermediate sections is radially opposite the first one of the curved or bent flanks, the second one of the curved or bent flanks and the third one of the radially outwardly extending straight flanks.

7. A ventilation tube system in accordance with claim 6, wherein the inner tube is under a prestress in an axial direction, which contracts the inner tube in the axial direction.

* * * * *